US012558391B2

(12) United States Patent
Von Metzinger et al.

(10) Patent No.: US 12,558,391 B2
(45) Date of Patent: Feb. 24, 2026

(54) **SUSTAINED RELEASE FORMULATION CONTAINING *ASPALATHUS LINEARIS* EXTRACT**

(71) Applicant: Cape Peninsula University of Technology, Cape Town (ZA)

(72) Inventors: Jeanine Lucasta Von Metzinger, Kenridge (ZA); John Henry Neethling, Bellville (ZA); Josias H Hamman, Potchefstroom (ZA); Marilize Le Roes-Hill, Fish Hoek (ZA)

(73) Assignee: Cape Peninsula University of Technology, Cape Town (ZA)

( * ) Notice: Subject to any disclaimer, the term of this patent is extended or adjusted under 35 U.S.C. 154(b) by 763 days.

(21) Appl. No.: 17/763,774

(22) PCT Filed: Apr. 22, 2020

(86) PCT No.: PCT/IB2020/053802
§ 371 (c)(1),
(2) Date: Mar. 25, 2022

(87) PCT Pub. No.: WO2021/059027
PCT Pub. Date: Apr. 1, 2021

(65) Prior Publication Data
US 2022/0339231 A1 Oct. 27, 2022

(30) Foreign Application Priority Data
Sep. 25, 2019 (GB) ...................................... 1913827

(51) Int. Cl.
| | |
|---|---|
| *A61K 36/48* | (2006.01) |
| *A61K 9/00* | (2006.01) |
| *A61K 9/48* | (2006.01) |

(52) U.S. Cl.
CPC ............ *A61K 36/48* (2013.01); *A61K 9/0056* (2013.01); *A61K 9/4808* (2013.01); *A61K 9/485* (2013.01); *A61K 9/4858* (2013.01); *A61K 9/4866* (2013.01)

(58) Field of Classification Search
None
See application file for complete search history.

(56) References Cited

U.S. PATENT DOCUMENTS

| | | | |
|---|---|---|---|
| 2006/0159748 A1* | 7/2006 | Jain ...................... | A61K 9/2077 514/212.07 |
| 2009/0053310 A1* | 2/2009 | Pilgaonkar ............. | A61K 47/12 514/474 |

(Continued)

FOREIGN PATENT DOCUMENTS

| | | |
|---|---|---|
| WO | WO 2010/078192 A2 | 7/2010 |
| WO | WO-2017037628 A1 * | 3/2017 |

OTHER PUBLICATIONS

Belwal, T., Dhyani, P., Bhatt, I. D., Rawal, R. S. & Pande, V. 2016. Optimization extraction conditions for improving phenolic content and antioxidant activity in *Berberis asiatica* fruits using response surface methodology (RSM). Food Chemistry, 207, 115-124.

(Continued)

*Primary Examiner* — Dominic Lazaro
(74) *Attorney, Agent, or Firm* — Herbert Smith Freehills Kramer (US) LLP

(57) ABSTRACT

A multi-unit pharmaceutical composition comprising an immediate release component comprising a polyphenol-containing *Aspalathus linearis* extract and one or more pharmaceutically acceptable excipients, and a sustained release component comprising a polyphenol-containing *Aspalathus linearis* extract and one or more pharmaceutically acceptable excipients, wherein the composition pro- (Continued)

................ pH 1 vides a substantially linear polyphenol release profile over a predetermined period, for example about 8 hours.

16 Claims, 9 Drawing Sheets

(56)                    References Cited

U.S. PATENT DOCUMENTS

| | | | | |
|---|---|---|---|---|
| 2014/0135350 A1* | 5/2014 | Ni | ............................ | A61P 17/04 |
| | | | | 514/265.1 |
| 2015/0094322 A1* | 4/2015 | Riel | ........................ | A61K 47/36 |
| | | | | 514/460 |
| 2017/0340570 A1* | 11/2017 | Meyer | .................. | A61K 9/0004 |

OTHER PUBLICATIONS

Singleton, V. L. & Rossi, J. A. 1965. Colorimetry of Total Phenolics with Phosphomolybdic-Phosphotungstic Acid Reagents. American Journal of Enology and Viticulture, 16, 144-158.

USP. 2016d. United States Pharmacopeia 711: Dissolution. North Bethesda, Maryland, United States: United States Pharmacopeia Convention, Official Dec. 1, 2011.

Ihsan Iswaldi et al: "Identification of phenolic compounds in aqueous and ethanolic rooibos extracts, by HPLC-ESI-MS (TOF/IT)", Analytical and Bioanalytical Chemistry, vol. 400, No. 10, Apr. 21, 2011, pp. 3643-3654, XP019924898, table 1.

Lauro Maria Rosaria et al: "Fast- and Slow-release Tablets for Oral Administration of Flavonoids: Rutin and Quercetin", Drug Development and Industrial Pharmacy, vol. 28, No. 4, Apr. 1, 2002, pp. 371-379, XP008070189, ISSN: 0363-9045, DOI:10.1081/DDC-120002998, tables 2,3.

Jan. 1, 2008 (Jan. 1, 2008), Pharmaceutical Manufacturing Handbook: Production and Processes, John Wiley & Sons, Incorporated, 2008, XP002779928, tables 2,3.

Ying-Huan Li et al., Modulation of combined-release behaviors form a novel "tablets-in-capsule system", Journal of Controlled release, Elsevier, vol. 95, No. 3, Mar. 24, 2004, pp. 381-389 table 1, 2.

PCT International Search Report for application No. PCT/IB2020/053802 dated Jul. 8, 2020.

* cited by examiner

SUSTAINED RELEASE FORMULATION CONTAINING *ASPALATHUS LINEARIS* EXTRACT

CROSS-REFERENCE TO RELATED APPLICATIONS

This application is a national stage application, filed under 35 U.S.C. § 371, of International Patent Application No. PCT/IB2020/053802 filed on Apr. 22, 2020, which claims the benefit of Great Britain Application No. 1913827.0, filed Sep. 25, 2019, each of which is incorporated by reference herein in its entirety.

FILED OF THE INVENTION

This invention relates to a sustained release formulation containing an extract of fermented *Aspalathus linearis* (Rooibos). In particular, the invention relates to a multi-unit pharmaceutical composition containing Rooibos in which certain components provide immediate release and other components provide sustained release of the polyphenols in the extract after oral administration.

BACKGROUND TO THE INVENTION

The past decade has shown an exponential increase in the number of research studies reporting on the health benefits of the South African indigenous herbal tea, Rooibos (also referred to as Red Bush in other countries) from the plant *Aspalathus linearis*. However, when orally consumed some of the active ingredients of Rooibos (e.g. phenolic compounds) have relatively short plasma half-lives due to rapid elimination and poor absorption in the intestine. The body's exposure to the beneficial components of Rooibos is therefore short-lived, limiting the proposed health benefits if it is not consumed regularly during the course of the day. Therefore, several cups of this herbal tea need to be consumed at regular intervals (e.g. six cups evenly spread during a day) for optimum effects.

A need therefore exists to develop a sustained release dosage form that is capable of releasing the phytochemical components of Rooibos over an extended period of time after oral administration in order to prolong the proposed health benefits to the consumer after a single dose.

WO-2017/037628 entitled Rooibos Preparation is an international application in the name of the applicant of the present application. WO 2017/037628 sets out that such a composition and release profile is desirable, but fails to teach the skilled person how this can be achieved. The specification does not provide any information or examples of pharmaceutical formulations that would satisfy this desire, nor does it propose how the skilled person can go about formulating such compositions.

It is an object of this invention to provide a modified-release, multi-unit pharmaceutical composition for a Rooibos extract, for example a fermented Rooibos extract, that provides immediate release of a loading dose and sustained release of a maintenance dose over a predetermined and extended period of time. It is a further object of the invention to provide for a pharmaceutical composition having such a release profile, that releases more than about 80% of polyphenols contained in the composition, over the predetermined and extended period of time.

SUMMARY OF THE INVENTION

In accordance with a first aspect of the present invention there is provided a multi-unit pharmaceutical composition comprising an immediate release component comprising a polyphenol-containing *Aspalathus linearis* extract and one or more pharmaceutically acceptable excipients, and a sustained release component comprising a polyphenol-containing *Aspalathus linearis* extract and one or more pharmaceutically acceptable excipients, wherein the composition provides a substantially linear polyphenol release profile over a predetermined period.

In one embodiment, the *Aspalathus linearis* extract is a fermented extract.

In one embodiment, the pharmaceutically acceptable excipients in the immediate release component include a filler.

Preferably, the filler is sodium bicarbonate.

In one embodiment, the sodium bicarbonate is present at a concentration of about 24% (% w/w) or less in the immediate release component.

In one embodiment, the pharmaceutically acceptable excipients in the immediate release component include a disintegrant.

Preferably, the disintegrant is sodium starch glycolate, sodium carboxymethyl cellulose, or mixtures thereof.

In one embodiment, the pharmaceutically acceptable excipients in the sustained release component include a binder.

Preferably, the binder is vinylpyrrolidone-vinyl acetate.

In one embodiment, the pharmaceutically acceptable excipients in the sustained release component include rate-controlling polymer excipients.

Preferably, the rate-controlling polymer excipients is selected from polyvinyl acetate-polyvinylpyrrolidone, and hypromellose-lactose monohydrate, and mixtures thereof.

In one embodiment, the rate-controlling polymer excipients is polyvinyl acetate and polyvinylpyrrolidone (approximately 80:20 ratio) which is present at a concentration of about 16% to about 22% (% w/w) in the sustained release component.

In one embodiment, the rate-controlling polymer excipients is hypromellose and lactose monohydrate (approximately equal parts) which is present at a concentration of about 15% to about 21% (% w/w) in the sustained release component.

In one embodiment, the pharmaceutically acceptable excipients in the immediate and sustained release components include a lubricant.

Preferably, the lubricant is magnesium stearate.

Preferably, the predetermined period is about 6 hours to about 10 hours.

More preferably, the predetermined period is about 7 hours to about 9 hours.

Most preferably, the predetermined period is about 8 hours.

In one embodiment, the pharmaceutical composition is a mini-tablet-in-capsule system.

In one embodiment, the pharmaceutical composition contains 2 immediate release components and 8 sustained release components.

In one embodiment, each immediate release and sustained release component contains about 60% to about 80% (% w/w) *Aspalathus linearis* extract.

In one embodiment, each immediate release component has about the following composition, by mass percentage:
*Aspalathus linearis* extract: 66.7%,
Sodium bicarbonate: 24.3%,
Sodium starch glycolate: 8%, and
Magnesium stearate: 0.5%.

In one embodiment, each sustained release component has about the following composition, by mass percentage:

Aspalathus linearis extract: 80%,
Vinylpyrrolidone-vinyl acetate: 3.5%,
Hypromellose and lactose monohydrate (in equal parts): 15.25%,
Silica: 1%, and
Magnesium stearate: 0.25%.

In another embodiment, each sustained release component has about the following composition, by mass percentage:

Aspalathus linearis extract: 80%,
Vinylpyrrolidone-vinyl acetate: 3.5%,
Polyvinyl acetate/polyvinylpyrrolidone (80:20): 15.25%,
Silica: 1%, and
Magnesium stearate: 0.25%.

According to a second aspect of the present invention there is provided a method for providing a sustained release of polyphenols from an Aspalathus linearis source over a predetermined time period in a subject, the method comprising administering a multi-unit pharmaceutical composition according to the first aspect of the invention to the subject, wherein the sustained release of polyphenols occurs according to a substantially linear polyphenol release profile.

According to another aspect of the present invention there is provided a multi-unit pharmaceutical composition comprising of two different release profile components, a first immediate release component comprising a polyphenol-containing Aspalathus linearis extract and one or more pharmaceutically acceptable excipients, and a second sustained release component comprising a polyphenol-containing Aspalathus linearis extract and one or more pharmaceutically acceptable excipients, wherein the multi-unit composition provides a substantially linear polyphenol release profile over a predetermined period.

BRIEF DESCRIPTION OF THE FIGURES

The invention will now be described in more detail with reference to the following non-limiting embodiments and figures in which.

DETAILED DESCRIPTION OF THE INVENTION

Figure 1:
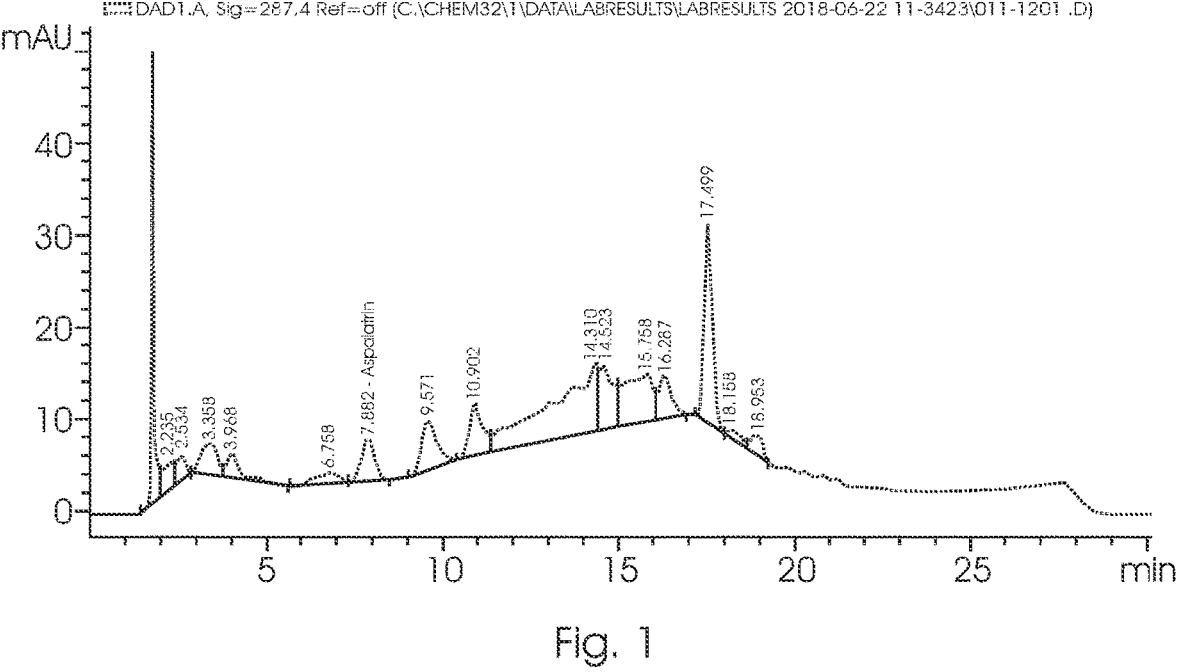
FIG. 1 shows a chromatogram for the analysis of the Rooibos extract used in the examples, monitored at 287 nm.

Before any embodiments of the invention are explained in detail, it is to be understood that the invention is not limited in its application to the details of construction and the arrangement of components set forth in the following description or exemplified in the following examples.

The invention is capable of other embodiments and of being practiced or of being carried out in various ways. Also, it is to be understood that the phraseology and terminology used herein is for the purpose of description and should not be regarded as limiting. The use of "including", "comprising," or "having" and variations thereof herein is meant to encompass the items listed thereafter and equivalents thereof as well as additional items. The terminology includes the words specifically mentioned above, derivatives thereof, and words of similar import. It is noted that, as used in this specification, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Formulation of Dosage Forms

Modified release drug delivery systems refer to dosage forms that release the active components at a pre-determined rate for sustained release over an extended period of time and/or at a pre-determined site in the gastro-intestinal tract. Tablets are commonly used as modified oral drug delivery systems.

Conventional dosage forms such as immediate release tablets were initially formulated to provide active pharmaceutical ingredients in sufficiently high concentrations in the areas where absorption can take place to result in therapeutic blood levels. The active ingredients are therefore released as quickly as possible after administration in the gastrointestinal tract from where it is absorbed-into the systemic circulation. However, any active ingredient absorbed into the systemic circulation is eliminated by means of metabolism and renal excretion and therefore its concentration will decrease to below therapeutic levels if another dose is not administered. Rapid elimination of any compound results in a short half-life of that compound. This also causes a relatively large fluctuation of the compound's concentration in systemic circulation between consecutive doses.

Sustained release type tablets are dosage forms that release the drug load slowly over an extended period of time. The aim with sustained release dosage forms is to maintain the drug at therapeutic levels in the systemic circulation for a longer time than is possible with immediate release formulations. This is important for drugs with relatively short half-lives and can assist to overcome fluctuations in the concentration of the drugs in the systemic circulation between drug doses.

Pharmacologically active compounds are almost never administered in their pure form, but are usually formulated in dosage forms that consist of both the active ingredient and adjuvants referred to as excipients.

Excipients are substances, other than the active drug substances of finished dosage form, which have been appropriately evaluated for safety and are included in a dosage form to aid the processing of the drug delivery system during its manufacture, protect the active compound, support the tablet, enhance stability and bioavailability, patient acceptability and assist in product identification. However, progress in technology has led to the development of excipients that fulfil specific functions in modern dosage forms. These functions range from improving the manufacturability to enhanced delivery of the active ingredient.

Excipients can be divided into different categories based on their function in tablet formulation. Fillers or diluents are added to the powder mixture to add bulk in terms of volume and mass to ensure the correct size of the tablet is achieved. Fillers should be chemically inert, non-hygroscopic and biocompatible with the drug, have good compatibility properties, have an acceptable taste and be cost-effective. In some cases, a single filler cannot fulfil all the needs and more than one filler can then be used in a single tablet formulation. Common fillers include sugars, cellulose, calcium carbonate and calcium phosphate.

Disintegrants are added to the tablet formulation to assist with the breakup of the tablet after administration when it is exposed to liquid in the gastrointestinal tract. This breakup results in small particles that allow for faster dissolution. Disintegrants have different mechanisms of action to cause the breakup of tablets, which include swelling, exothermic wetting reactions, gas production, particle repulsion and particle deformation recovery. Common disintegrants used include starches, cellulose, cross-linked polyvinylpyrrolidone, sodium starch glycolate, sodium carboxymethyl cellulose as well as carbonate and bicarbonate salts.

Binders are added to the tablet formulation to ensure that the final product has adequate mechanical strength. Binders can be divided into dry binders (powder form) and liquid binders (solutions of binders in adequate solvents). Dry binders are added to the powder mixture before direct compaction or before granulation. Liquid binders are added to the powder mixture during granulation. Common binders used are starches, sucrose, gelatin and polymers such as polyvinylpyrrolidone, polyethylene glycol and cellulose derivatives such as hydroxypropyl methylcellulose.

Glidants are added to the tablet formulation to improve the powder flow properties. It is often added to direct compaction tablet formulations, but can also be added during granulation. Commonly used glidants include colloidal silica, talc and magnesium stearate.

Lubricants reduce friction between the solid powder particles and the die and punches of the tablet press during compaction and ejecting of the tablet. This can be achieved by either fluid lubrication or boundary lubrication. Fluid lubrication requires a fluid layer between the solid and the die surface. This type of lubricant is not often used in tablet production. Boundary lubricants are usually very fine powders that form a thin surface layer that reduce the shear forces between the tablet and the die. Stearic acid and magnesium stearate are the most commonly used lubricants.

Single-unit dosage forms consist of a single unit containing the complete dose of the active ingredient, usually a tablet or a capsule. Multiple-unit or multi-unit dosage forms comprise of more than one sub-unit, each containing a portion of the dose. Examples of multi-unit dosage forms include granules, beads, pellets, microspheres or mini-tablets, which are filled into hard gelatin capsules or sachets or can be compressed into tablets. The drug content of all the sub-units amounts to the total dose of the dosage form. Hard gelatin capsules present a convenient packaging format for the sub-units of a multiple-unit dosage form. When the hard gelatin capsules are filled with the sub-units, it results in a more accurate and consistent dosing of the multiple-units. When this multiple-unit dosage form is administered via the oral route, the capsule shell dissolves in the stomach and releases the sub-units. Mini-tablet-in-capsule systems are advantageous dosage forms that merge the benefits of traditional tablet production with the benefits of multiple-unit dosage forms.

Mini-tablet-in-capsule systems are multiple-unit drug delivery systems where a number of mini-tablets are filled into hard gelatin capsules. Mini-tablets are produced using normal tablet production methods and are then loaded into hard gelatine capsules.

EXAMPLES

The invention is exemplified by way of the examples that follow.

Commercially available fermented Rooibos (*Aspalathus linearis*) extract, spray dried and in powder form, was used in all the following examples. Pharmaceutical excipients were used as obtained from suppliers.
Polyphenols Determination Even though Rooibos contains many phenolic compounds, the polyphenol content will be quantified based on a total polyphenols assay.

The total polyphenols assay is a modified method based on the method of Singleton and Rossi (1965), as published by Belwal et al. (2016), which method is hereby incorporated by reference. In the analysis that follows, the Folin Ciocalteu reagent was used (together with gallic acid as the standard) to measure total polyphenols of a sample using 96 well plates and a UV/Vis plate reader.

The reagents were prepared as described below. A working Folin Ciocalteu reagent was prepared by dilution of the Folin Ciocalteu reagent (Sigma-Aldrich) in a ratio 1:10 with distilled water. A 7.5% (w/v) sodium carbonate solution was prepared by dissolving 7.5 g of $Na_2CO_3$ (Sigma-Aldrich) in distilled water and made up to a final volume of 100 ml. Gallic acid standards were prepared in 10% (v/v) ethanol solution with a concentration range of 0 to 500 mg/l and used to prepare the standard curve.

The assay was performed by placing 25 μl of the blank, standard or sample into the respective wells of a 96 well plate. A volume of 125 μl of working reagent was added to each well and incubated at room temperature for 5 min. Then 100 μl $Na_2CO_3$ was added to each well and incubated for 2 hours at room temperature. The absorbance of each well was measured at 765 nm on a Thermoscientific Multiskan Spectrum plate reader. The average total polyphenols of the Rooibos extract was 325.98 mg gallic acid equivalents (GAE/g) per gram extract.

Figure 2:
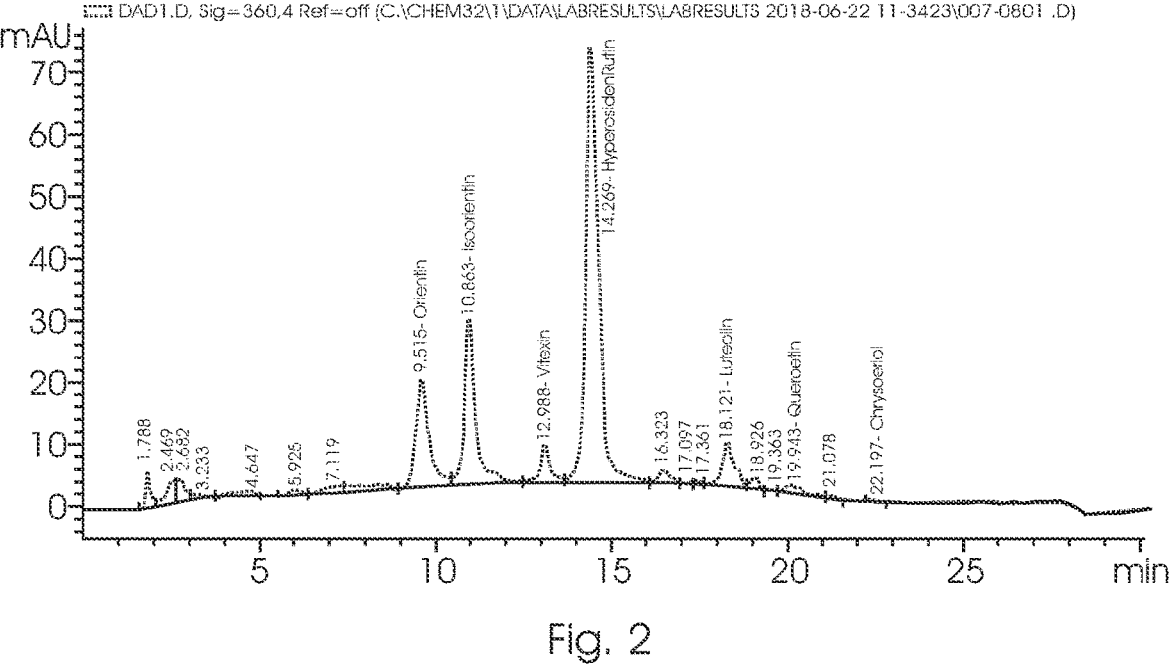
FIG. 2 shows a chromatogram for the analysis of the Rooibos extract used in the examples, monitored at 360 nm.

The main individual polyphenol make-up was analysed by HPLC. The HPLC analyses were performed using an Agilent 1200 HPLC system (Santa Clara, USA) equipped with an auto-sampler and a diode array detector. A YMC-Pack Pro C18 RS (5 μm) 150×4.6 mm (YMC America, Allentown, USA) reverse phase column was used for the separation of the compounds and a 10 μl injection volume. The mobile phase employed was a gradient of (A) 2% v/v formic acid and (B) 100% methanol (Merck) at a flow rate of 0.5 ml/min. Samples were filtered with 0.22 μm syringe filters before being diluted with distilled water. The chromatograms were constructed by monitoring the absorbance at 287 nm and 360 nm. The results are shown in FIG. 1 and FIG. 2.

Tablet Formulation and Production

The aim of the formulation investigations was to produce a pharmaceutical formulation that can deliver 400 mg Rooibos extract (approximately 120 mg GAE polyphenols) over an extended period of time of about 6 to about 10 hours (e.g. about 7 to about 9 hours, or about 8 hours). The inventors investigated formulations that seeks to achieve this aim by having an initial loading dose of about 80 mg that is immediately released, followed by a linear or substantially linear release of a maintenance dose of about 320 mg. The target value of polyphenols released from the pharmaceutical composition is at least about 80%, preferably at least about 85%, more preferably at least about 90%.

As used herein, the term "substantially linear polyphenol release profile" should be understood to mean a profile in which the coefficient of determination for a linear regression line fitted to the amount of polyphenols released from the pharmaceutical composition over the period of release is at least about 90%, with a total release of polyphenols from the composition of at least about 80% in about 8 hours. Preferably, the total release of polyphenols from the composition is about 85%, more preferably about 90% in about 8 hours.

In the examples that follow, examples that fall outside the scope of a substantially linear polyphenol release profile are comparative examples.

In one example, a mini-tablet-in-capsule system was investigated. The system was designed to contain two immediate release tablets, and eight sustained release tablets each containing about 40 mg Rooibos extract.

Different immediate release tablets were formulated using different fillers namely sodium bicarbonate, microcrystalline cellulose (for example Avicel®), calcium hydrogen phosphate dihydrate (for example Emcompress®) and agglomerated alpha-lactose monohydrate (for example Tablettose®). Different disintegrants were included in the formulations namely sodium starch glycolate (for example Explotab®), and croscarmellose sodium (for example Ac-Di-Sol®). Magnesium stearate was used as a lubricant.

The different sustained release tablets were formulated using rate controlling polymer excipients namely polyvinyl acetate and polyvinylpyrrolidone (approximately 80:20 ratio) (for example Kollidon SR®) and hypromellose and lactose monohydrate (in equal parts) (for example, Retalac®), and HPMC (hydroxypropyl methylcellulose) or a 50/50 mixture of HPMC and Chitosan. Vinylpyrrolidone-vinyl acetate (for example Kollidon VA 64®) was used as a binder and magnesium stearate as lubricant.

Different immediate release mini-tablets were produced using different combinations of excipients as shown in Table 1, and these tablets were evaluated in terms of dissolution profiles.

TABLE 1

Compositions (% w/w) of different immediate release tablet formulations tested.

| Tablet ID | Rooibos extract | Magnesium stearate | Avicel ® | Emcompress ® | Tablettose ® | NaHCO₃ | Explotab ® | Ac-Di-Sol ® |
|---|---|---|---|---|---|---|---|---|
| A-1 | 61.5% | | 38.5% | | | | | |
| A-2 | 66.8% | | 30.5% | | | | | 2.7% |
| T-1 | 66.6% | 0.2% | | | 28.2% | | | 5% |
| T-2 | 66.5% | 0.2% | | | 23.3% | | | 10% |
| T-3 | 66.7% | 0.15% | | | 32.15% | | | 1% |
| T-4 | 66.7% | 0.15% | | | 29.15% | | 4% | |
| T-5 | 66.7% | 0.15% | | | 25.15% | | 8% | |
| M-1 | 66.7% | 0.1% | | 32.3% | | | | |
| M-2 | 66.7% | 0.1% | | 31.3% | | | | 1% |
| M-3 | 66.7% | 0.1% | | 24.3% | | | 8% | |
| M-4 | 66.7% | 0.1% | | 23.3% | | | 8% | 1% |
| N-1 | 66.7% | 1% | | | | 24.3% | 8% | |

The different sustained release mini-tablets were formulated as outlined in Table 2 below. The formulations were specifically evaluated in terms of dissolution to find a matrix-type mini-tablet that released at least about 90% of the Rooibos extract content within a period of about 8 hours, but at a slower rate than the immediate release tablets.

TABLE 2

Compositions (% w/w) of different sustained release tablet formulations tested

| Tablet ID | Rooibos extract | Magnesium stearate | Kolidon VA64 ® | HPMC ® | Kolidon SR ® | Chitosan | Retalac ® | Silica | Talc |
|---|---|---|---|---|---|---|---|---|---|
| C-1 | 66.7% | 0.25% | 3.5% | 12.5% | 12.5% | | | | 4.55% |

TABLE 2-continued

Compositions (% w/w) of different sustained release tablet formulations tested

| Tablet ID | Rooibos extract | Magnesium stearate | Kolidon VA64 ® | HPMC ® | Kolidon SR ® | Chitosan | Retalac ® | Silica | Talc |
|---|---|---|---|---|---|---|---|---|---|
| H-1 | 61.5% | 0.2% | 3.5% | 32.3% | | | | | 2.5% |
| K-1 | 66.6% | 0.1% | 3.3% | | 30% | | | | |
| K-2 | 61.2% | 0.1% | 3.5% | | 35.2% | | | | |
| K-3 | 75% | 0.1% | 3.5% | | 21.4% | | | | |
| K-4 | 80% | 0.1% | 3.5% | | 16.4% | | | | |
| K-5 | 80% | 0.25% | 3.5% | | 16.25% | | | | |
| R-1 | 61.5% | 0.1% | 3.5% | | | | 34.9% | | |
| R-2 | 61.5% | 0.1% | 3.5% | | | | 33.9% | 1% | |
| R-3 | 75% | 0.1% | 3.5% | | | | 20.4% | 1% | |
| R-4 | 80% | 0.1% | 3.5% | | | | 15.4% | 1% | |
| R-5 | 80% | 0.25% | 3.5% | | | | 15.25% | 1% | |

The mass of Rooibos extract and excipients were calculated for the number of tablets to be produced for each formulation. The amount of extract and excipients were weighed and transferred into a vessel. The powder mixture was mixed in a Turbula® mixer (Willy A Bachofer, Switzerland) for a period of 2 minutes. A Korsch XP1 single stage tablet press (Korsch AG, Germany) was used with a 6 mm die and flat punches. The position of the bottom punch was set in such a way to obtain the intended mass and the travel of the top punch was adjusted to regulate the hardness and thickness of the tablet. Once the setup was complete for the correct mass and hardness of the mini-tablets, the tablet press was operated on automatic mode to produce tablets at a rate of 30 tablets per minute.

Disintegration

Six randomly selected mini-tablets were placed in the baskets of an Erweka ZT232 disintegration tester (Heidenstamm, Germany). The water bath of the apparatus was maintained at 37° C. A beaker with a volume of 1 L was filled with deionized water and placed in the water bath. The volume of distilled water was adjusted to ensure that the bottom of the basket was at least 15 mm submersed during the upwards stroke and the top of the basket was not submersed during the downward stroke. The basket was cycled up and down at a rate of 30 strokes per minute. The time was recorded until no visual fragment of the tablet was visible on the sieve in each cylinder. For immediate release mini-tablets, the tablet ideally should disintegrate in less than 15 minutes and for sustained release mini-tablets, the tablet should not disintegrate within 15 minutes. The timing of the immediate release tablets was stopped after 60 minutes.

Dissolution

For the active ingredient in a solid oral dosage form to be absorbed after administration, it must first dissolve in the gastro-intestinal fluid. Dissolution of the drug from the dosage form provides a concentration gradient in the liquid phase between the surface of the absorbing mucosa and the blood surrounding the gastro-intestinal tract. Dissolution continues to replace the drug molecules that are removed by means of absorption.

Dissolution testing aims to monitor the cumulative release of the active ingredient as a function of time. The data obtained is used to construct a dissolution curve or to calculate the rate of release of the active(s) from the dosage form. It is used extensively in the development of drug formulation, comparison of generic dosage forms and in quality control processes. The data obtained can be used to predict the bioavailability of the compounds.

Dissolution studies were performed using a Distek, Ink., Distek 2500 (NJ, USA) dissolution system in the USP apparatus II (paddle) configuration. All screening studies were performed in triplicate.

The stirring rate was 50 rpm and the system was maintained at 37° C. The initial dissolution medium was 600 ml, pH 1 (0.1M) HCl solution for two hours. The pH was then increased by adding 300 ml 0.2 M tri-sodium phosphate. If necessary, the pH was adjusted to 6.8 by the addition of a sufficient quantity of either 2 M HCl or 2 M NaOH. Samples were manually taken at predetermined intervals and the volume of solution removed was replaced with either 0.1 M HCl or phosphate buffer (USP, 2016). The samples were filtered through a 0.45 m syringe filter to remove any potential fragment of the undissolved tablets. These samples were analysed for total polyphenols and a dissolution profile was created by plotting percentage of the polyphenols released as a function of time.

Immediate release and sustained release mini-tablets were crushed and dissolved in 50 ml warm water before being analysed for the total polyphenol content and the main individual polyphenol concentrations. The dissolved tablets were aliquoted and diluted with distilled water for each assay. The total polyphenol assay was performed using the same methodology that was used for the analysis of the Rooibos extract discussed above.

The main individual polyphenol make-up of the immediate release and sustained release mini-tablets were analysed by HPLC. The analysis was performed as described above.

Results—Disintegration of Immediate Release Component

Table 3 lists the disintegration times for the different immediate release mini-tablet formulations. Six replicates were performed in each case. The initial Avicel® excipient formulation (A-1) exhibited a very long disintegration time and is therefore not acceptable. The tablets formed a jelly-like layer around it during the disintegration test. This jelly-like layer prevented water penetration and thus inhibited the disintegration of the tablets as the tablets dissolved rather than disintegrating.

Disintegration time was used to optimize the immediate release tablets. Ac-Di-Sol® is a disintegrant widely used in the pharmaceutical industry to increase disintegration of tablets and capsules. A concentration of 2.7% (w/w) Ac-Di-Sol® was added to the Avicel® formulation (A-1) resulting in a slight improvement in the disintegration time, but none of the tablets disintegrated within 30 minutes (A-2).

Emcompress® was used as an alternative excipient to replace Avicel®. It is water insoluble and produces dense, brittle tablets (Anon). Emcompress® was first used without any disintegrants (M-1). This resulted in tablets with a disintegration time of between 26 and 43 minutes, with 66% of the tablets disintegrating in less than 30 minutes. It was envisaged that the addition of disintegrants would speed up the disintegration of the tablets. The addition of 1% (w/w) Ac-Di-Sol® (M-2) increased the disintegration time to between 37 and 42.5 min. It was decided to investigate if another disintegrant may improve the disintegration of the tablets. The addition of 8% by weight Explotab® instead of Ac-Di-Sol® (M-3) increased the disintegration time to between 34 minutes and two tablets not disintegrating in 60 minutes. A combination of 8% (w/w) Explotab® and 1% (w/w) Ac-Di-Sol® (M-4) had a similar disintegration time to that of the Explotab® formulation. These results indicated that Emcompress®, even with disintegrants added, was not an ideal filler for the production of acceptable immediate release Rooibos tablets.

Emcompress® was replaced by Tablettose. The Ac-Di-Sol® ratio was increased to 5% (w/w) (T-1). This resulted in a better disintegration rate, but still three of the six tablets did not disintegrate within 30 minutes. The Ac-Di-Sol® ratio was increased to 10% w/w resulting in none of the tablets disintegrating in 30 minutes (T-2). This indicated that an increase in Ac-Di-Sol® did not decrease the disintegration time. The Ac-Di-Sol® concentration was further decreased to 1% w/w (T-3), which resulted in all six tablets disintegrating between 26.5 and 28.5 minutes. This was an improvement, but still did not produce tablets that could disintegrate within the generally acceptable time of 15 minutes.

The Ac-Di-Sol® was replaced by 4% (w/w) Explotab® (T-4) in the previously discussed formulation. This resulted in a disintegration time of between 25 and 38 minutes. The Explotab® was increased to 8% (w/w) (T-5), but there was a relatively low decrease in the disintegration time (26 to 33 minutes). These results suggested that a combination of Tablettose® and Explotab® or Ac-Di-Sol® was not an ideal combination to decrease the disintegration time.

From the results of the dissolution studies performed on the initial formulations and Emcompress® (M-1), it was observed that the dissolution rate increased more rapidly once the pH of the solution was increased. Sodium bicarbonate was investigated as an excipient to increase the pH around the surface tablet in an attempt to prevent the jelly-like layer and thus improve the penetration of water into the tablet. Without being bound by any particular theory, it was envisaged that this would allow the disintegrant to disintegrate the tablets more efficiently, and in doing so speed up the disintegration of the tablets. A formulation was prepared using 24.3% (w/w) sodium bicarbonate, 8% (w/w) Explotab® and 1% (w/w) magnesium stearate (N-1). Surprisingly, the mini-tablets disintegrated in less than 30 minutes, which was still more than the required 15 minutes.

TABLE 3

The disintegration times for the immediate release mini-tablet formulations.

| Tablet ID | Disintegration time (min) | | | | | |
|---|---|---|---|---|---|---|
| | 1 | 2 | 3 | 4 | 5 | 6 |
| A-1 | 38 | 45 | 45 | >60 | >60 | >60 |
| A-2 | 31.5 | 37 | 48 | 53 | 53 | >60 |
| T-1 | 26 | 30 | 30 | 31 | 38 | 43 |
| T-2 | 33 | 35 | 36 | 36 | 38 | 38 |
| T-3 | 26.5 | 27 | 28 | 28 | 28 | 28.5 |
| T-4 | 25 | 27 | 28 | 29 | 36 | 38 |

TABLE 3-continued

The disintegration times for the immediate release mini-tablet formulations.

| Tablet ID | Disintegration time (min) | | | | | |
|---|---|---|---|---|---|---|
| | 1 | 2 | 3 | 4 | 5 | 6 |
| T-5 | 26 | 28 | 29 | 30 | 33 | 33 |
| M-1 | 26 | 26 | 28 | 29 | 31 | 47 |
| M-2 | 37 | 38 | 39.5 | 40 | 42 | 42.5 |
| M-3 | 34 | 36 | 38 | 54 | >60 | >60 |
| M-4 | 33 | 34 | 59 | 59 | >60 | >60 |
| N-1 | 9 | 14 | 16 | 16 | 25 | 27 |

The disintegration times for all the sustained release mini-tablet formulations (formulations shown in Table 2) was in excess of 30 minutes, indicating that none of the sustained release mini-tablet formulations would disintegrate quickly after administration, which could contribute to a desired sustained release profile.

Results—Dissolution

The dissolution results are presented as the percentage of total polyphenols released from selected mini-tablet formulations or mini-tablet-in-capsule systems plotted as a function of time in line graphs. All tests were performed in triplicate.

Example 1

Figure 3:
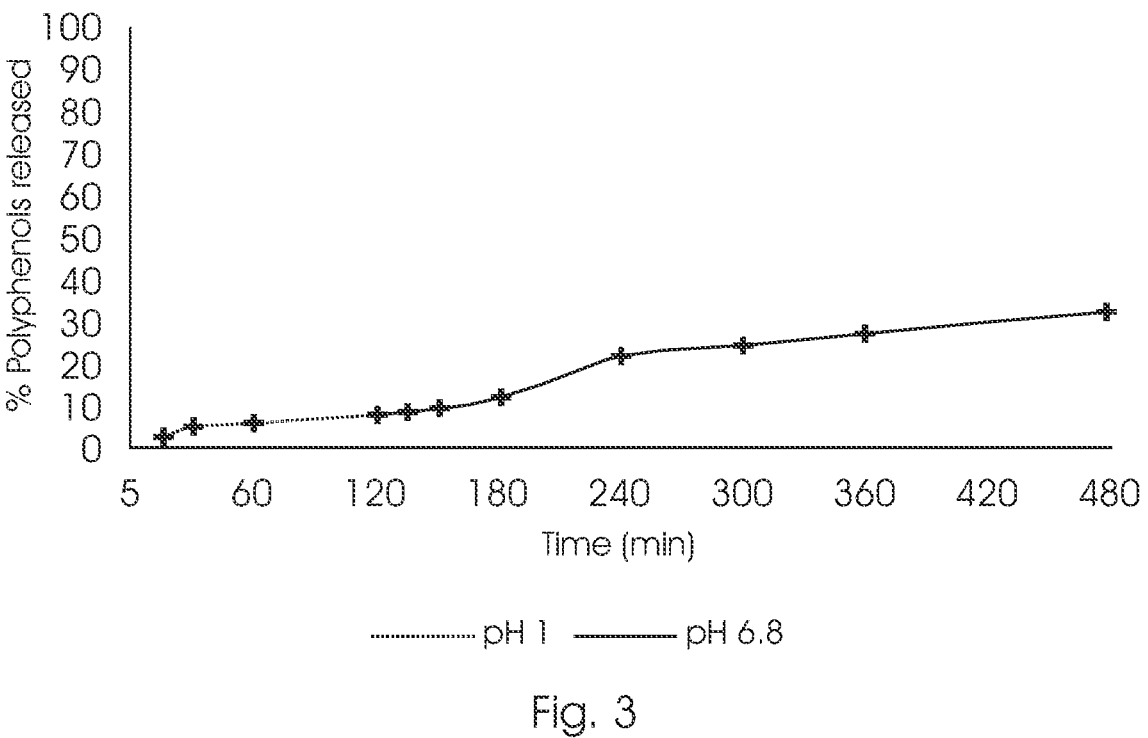
FIG. 3 shows a dissolution profile for a mini-tablet-in-capsule system containing two Avicel® 1 immediate release mini-tablets and eight Chitosan 1 sustained release mini-tablets.

The percentage release of total polyphenols plotted as a function of time for the mini-tablet-in-capsule system that contained two Avicel® immediate release mini-tablets and eight sustained release mini-tablets containing Chitosan (C-1) is shown in FIG. 3.

The dissolution results for the Chitosan formulation resulted in about 32.5% of polyphenols released in an 8 hour period.

Example 2

Figure 4:
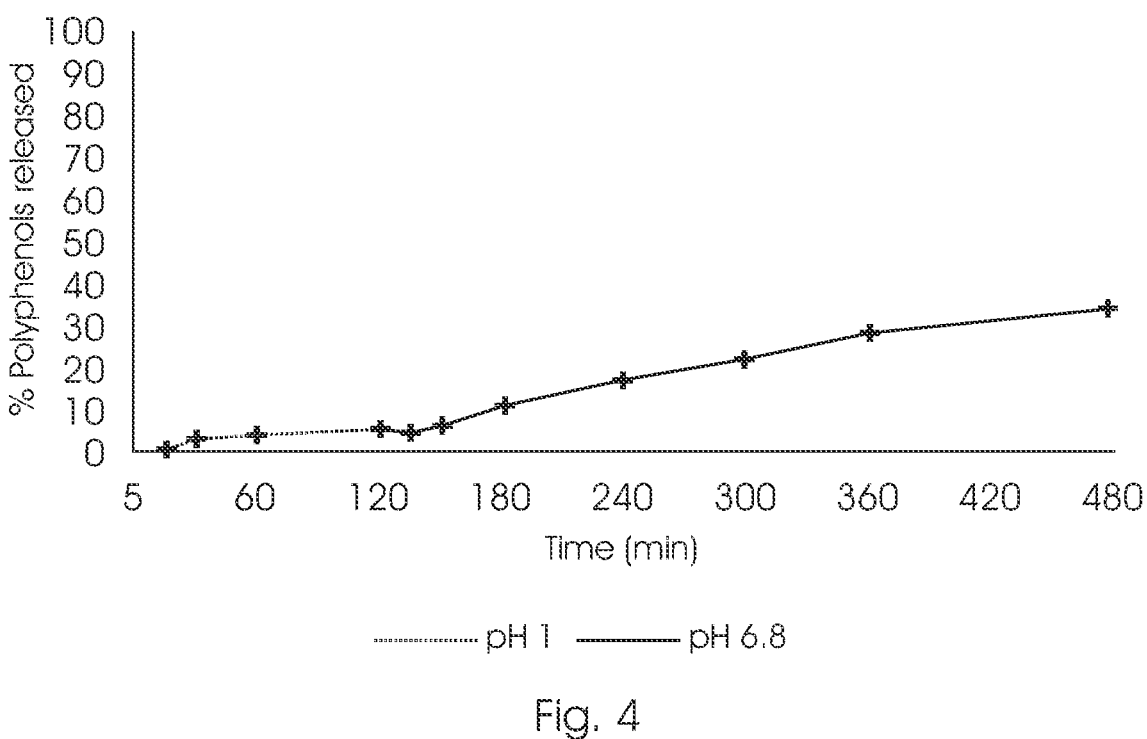
FIG. 4 shows a dissolution profile for a mini-tablet-in-capsule system containing two Avicel® 1 immediate release mini-tablets and eight HPMC 1 sustained release mini-tablets.

The percentage release of total polyphenols plotted as a function of time for the mini-tablet-in-capsule system that contained two Avicel® immediate release mini-tablets and eight HPMC sustained release mini-tablets (H-1) is shown in FIG. 4. The dissolution profile in FIG. 4 shows a relatively slow release over the first 2 hours, followed by a slightly faster release. No burst release effect can be observed and the total polyphenol release was only about 34% after 8 hours, which is below expectation and the target value. This mini-tablet-in-capsule formulation was therefore not considered acceptable for the purpose of providing a complete dose of Rooibos polyphenols within an 8 hour period.

Example 3

Figure 5:
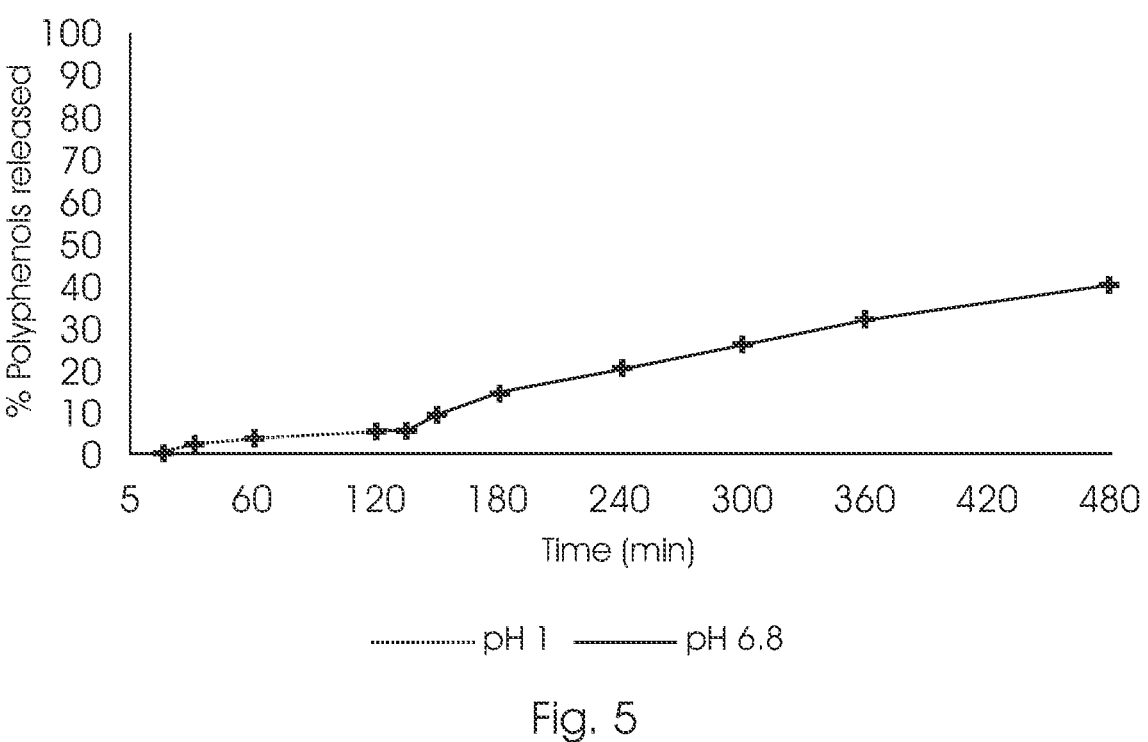
FIG. 5 shows a dissolution profile for a mini-tablet-in-capsule system containing two Avicel® 1 immediate release mini-tablets and eight Kollidon SR® 1 sustained release mini-tablets.

The percentage release of total polyphenols plotted as a function of time for the mini-tablet-in-capsule system that contained two Avicel® immediate release mini-tablets and eight sustained release mini-tablets made of 30% (w/w) polyvinyl acetate and polyvinylpyrrolidone (approximately 80:20 ratio) (Kollidon SR®, K-1) is shown in FIG. 5. The dissolution profile in FIG. 5 shows a relatively slow release over the first 2 hours (acidic environment), followed by a slightly faster release over the next 6 hours (neutral environment). No burst release effect can be observed and the total polyphenol release was only 40% after 8 hours. This was a slight improvement over the Chitosan-containing formulation (Example 1), but the total release was still below the target value.

Example 4

Figure 6:
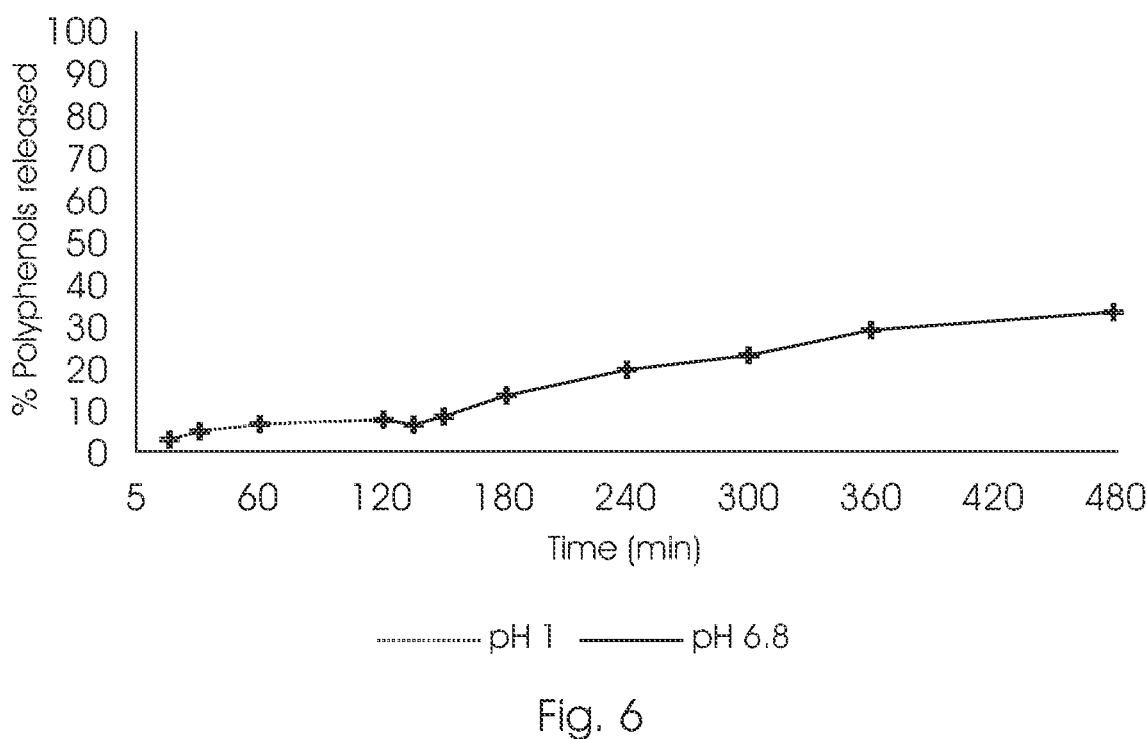
FIG. 6 shows a dissolution profile for a mini-tablet-in-capsule system containing two Avicel® 1 immediate release mini-tablets and eight Kollidon SR® 2 sustained release mini-tablets.

The percentage release of total polyphenols plotted as a function of time for the mini-tablet-in-capsule system that contained two Avicel® immediate release mini-tablets and eight sustained release mini-tablets made of 35.2% (w/w) polyvinyl acetate and polyvinylpyrrolidone (approximately 80:20 ratio) (Kollidon SR®, K-2) is shown in FIG. 6. The dissolution profile in FIG. 6 shows a relatively slow release over the first 2 hours (acidic environment), followed by a slightly faster release over the next 6 hours (neutral environment). No burst release effect can be observed and the total polyphenol release was only about 33.6% after 8 hours. This was a decrease in the total amount released when compared to the Kollidon SR® 1 formulation (Example 3), indicating that an increase in the Kollidon SR® concentration in the formulation results in a lowered rate of dissolution.

Example 5

Figure 7:
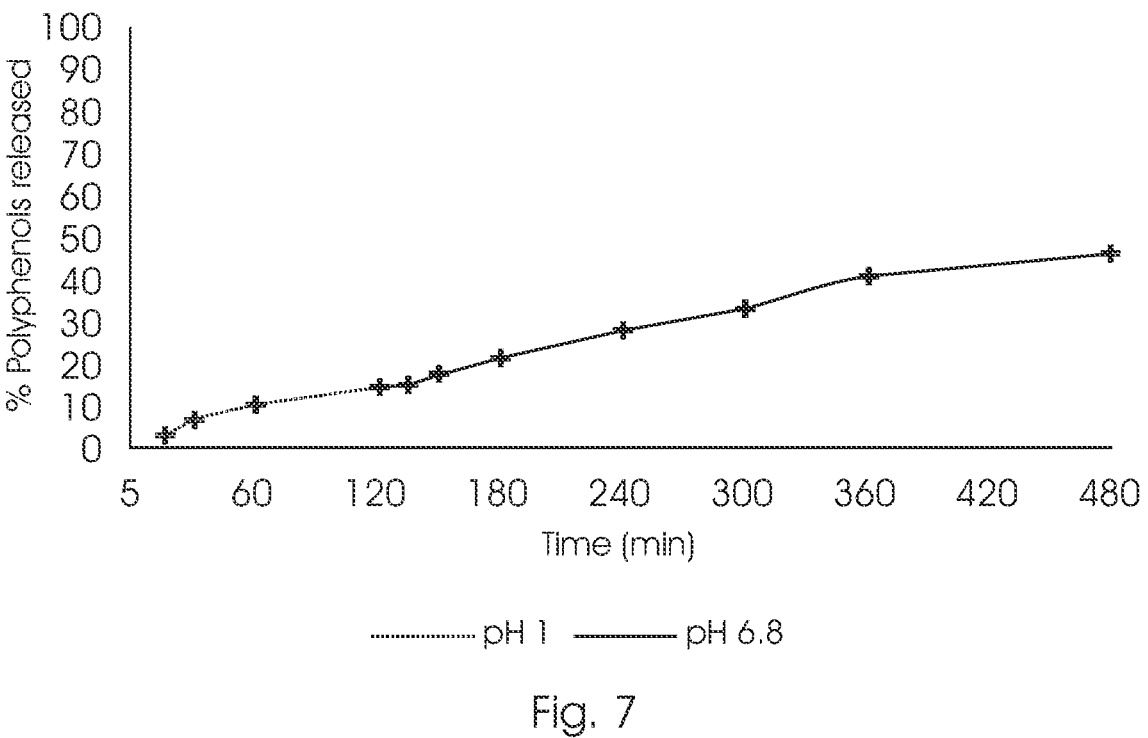
FIG. 7 shows a dissolution profile for a mini-tablet-in-capsule system containing two Avicel® 1 immediate release mini-tablets and eight Retalac® 1 sustained release mini-tablets.

The percentage release of total polyphenols plotted as a function of time for the mini-tablet-in-capsule system that contained two Avicel® immediate release mini-tablets and eight sustained release mini-tablets made of 34.9% (w/w) hypromellose and lactose monohydrate (in equal parts) (Retalac®, R-1) is shown in FIG. 7. The dissolution profile in FIG. 7 shows a relatively slow release over the first 2 hours (acidic environment), followed by a slightly faster release over the next 6 hours (neutral environment). No burst release effect can be observed and the total polyphenol release was only about 46% after 8 hours. This was an improvement on the Chitosan-containing formulation (Example 1), but the total release was still below the target value.

Example 6

Figure 8:
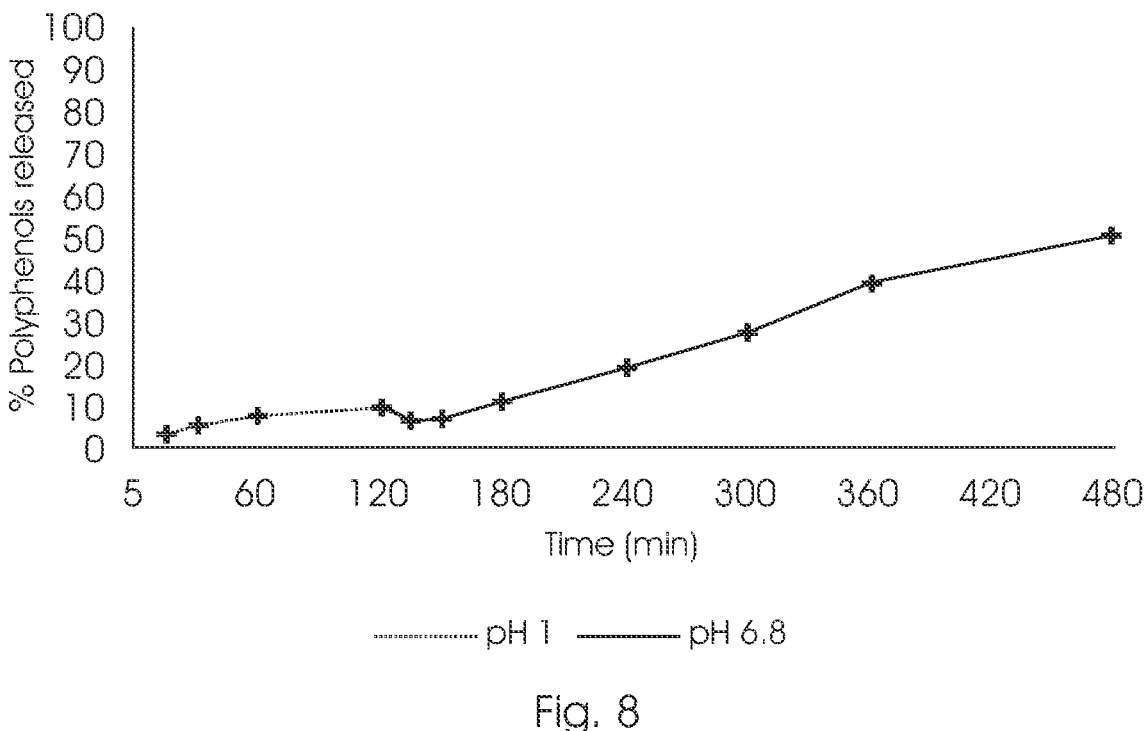
FIG. 8 shows a dissolution profile for a mini-tablet-in-capsule system containing two Avicel® 1 immediate release mini-tablets and eight Retalac® 2 sustained release mini-tablets.

The percentage release of total polyphenols plotted as a function of time for the mini-tablet-in-capsule system that contained two Avicel® immediate release mini-tablets and eight contained sustained release mini-tablets made of 33.9% (w/w) hypromellose and lactose monohydrate (in equal parts) and 1% silica (Retalac®, R-2) is shown in FIG. 8. The dissolution profile in FIG. 8 shows a relatively slow release over the first 2 hours (acidic environment), followed by a slightly faster release over the next 6 hours (neutral environment). No burst release effect can be observed and the total polyphenol release was only about 50% after 8 hours. This was a slight improvement on the Retalac® 1 formulation (Example 5), indicating that the addition of silica improved the dissolution.

Due to the higher percentage of polyphenol release obtained with the Kollidon SR® and Retalac® containing formulations (K-1, K-2, R-1, R-2), they were chosen to be further optimised. The Kollidon SR® 1 formulation (Example 3) had released a higher percentage of the Rooibos polyphenols in the 8 hours when compared to the Kollidon SR® 2 formulation (Example 4), which indicated that a decrease in the quantity of Kollidon SR® in the formulation could increase the dissolution rate and also the total polyphenol amount released over a period of 8 hours.

Example 7

Figure 9:
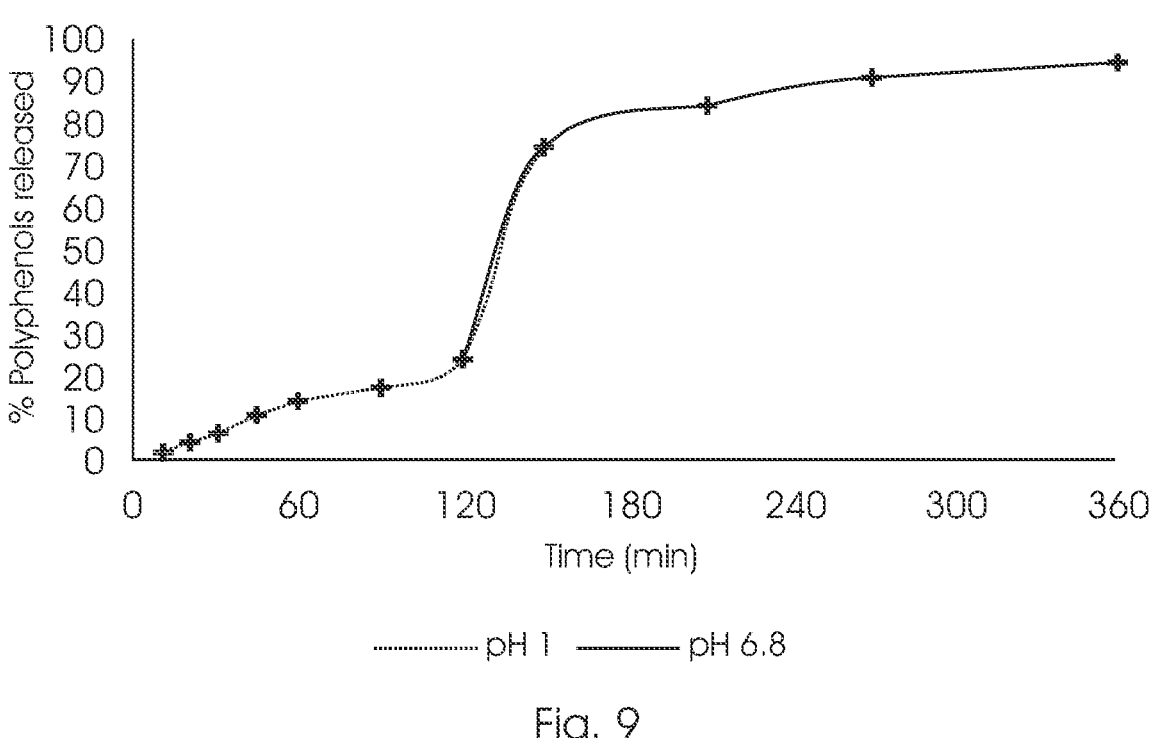
FIG. 9 shows a dissolution profile for Emcompress® 1 immediate release mini-tablets.

The percentage release of total polyphenols plotted as a function of time for immediate release mini-tablets (i.e. for loading dose) containing 32.3% (w/w) Emcompress® (M-1) is shown in FIG. 9. A burst release effect can clearly be observed when the pH was changed from acidic (pH 1) to neutral (pH 6.8) during the time period of 120 to 160 minutes. A total of about 70.6% of the polyphenols was released in the 4 hours following the change in pH. This indicates that the dissolution of the Rooibos polyphenols from this particular formulation is pH dependent.

Example 8

Figure 10:
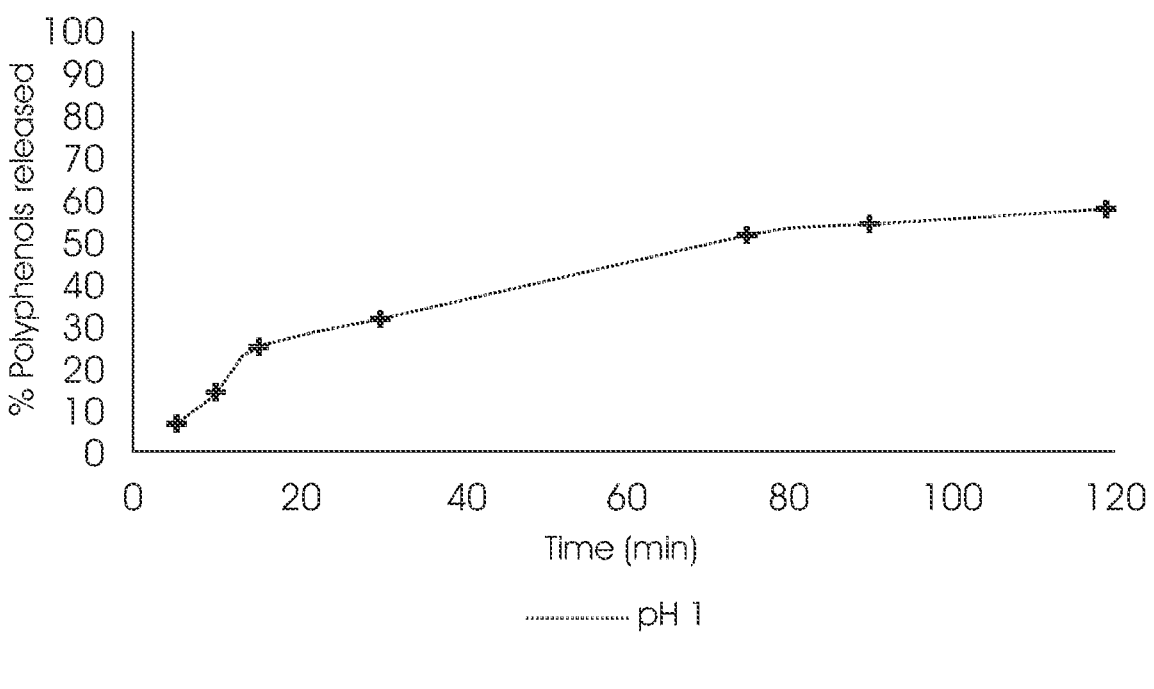
FIG. 10 shows a dissolution profile for sodium bicarbonate immediate release mini-tablets.

The percentage release of total polyphenols plotted as a function of time for immediate release mini-tablets containing $NaHCO_3$ (N-1) as the main excipient is shown in FIG. 10. The dissolution profile in FIG. 10 shows a fast, steady release over the first 2 hours (acidic environment). This was a major and surprising improvement over the Emcompress® 1 formulation, which only released about 20% of the polyphenols, to a polyphenol release of about 57%, in the acid solution within the 2 hour period.

This result confirmed once again that the dissolution of the Rooibos polyphenols is pH dependent and that by increasing the pH surrounding the mini-tablet the dissolution rate was increased.

Therefore, based on the example containing sodium bicarbonate, it is envisaged that the immediate release component can comprise from about 15% to about 35%, preferably from about 20% to about 30%, and most preferably about 24% (w/w) sodium bicarbonate.

Example 9

Figure 11:
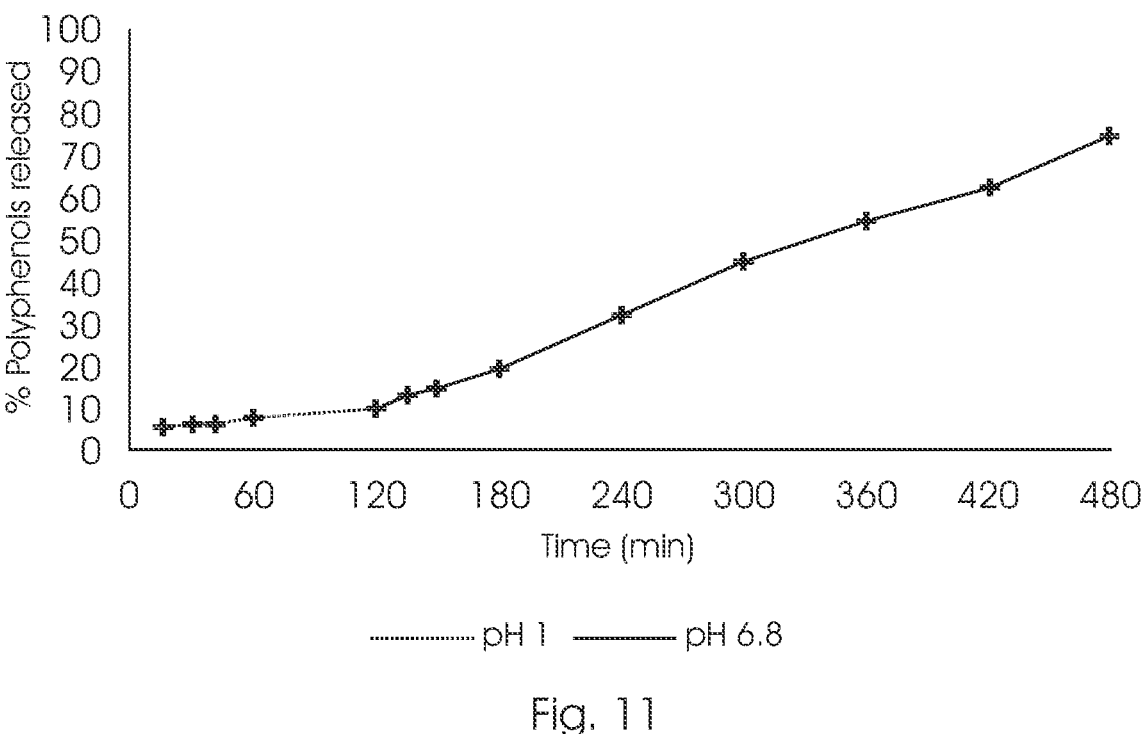
FIG. 11 shows a dissolution profile for Kollidon SR® 3 sustained release mini-tablets.

The percentage release of total polyphenols plotted as a function of time for sustained release mini-tablets made of 21.4% (w/w) polyvinyl acetate and polyvinylpyrrolidone (approximately 80:20 ratio) (Kollidon SR®, K-3) is shown in FIG. 11. The dissolution profile in FIG. 11 shows a relatively slow release over the first 2 hours (acidic environment) followed by a faster release over the next 6 hours (neutral environment). The total polyphenol release was about 71% after 8 hours. This was an increase in the total amount of polyphenols released when compared to the Kollidon SR® 1 formulation (K-1) of Example 3.

Example 10

Figure 12:
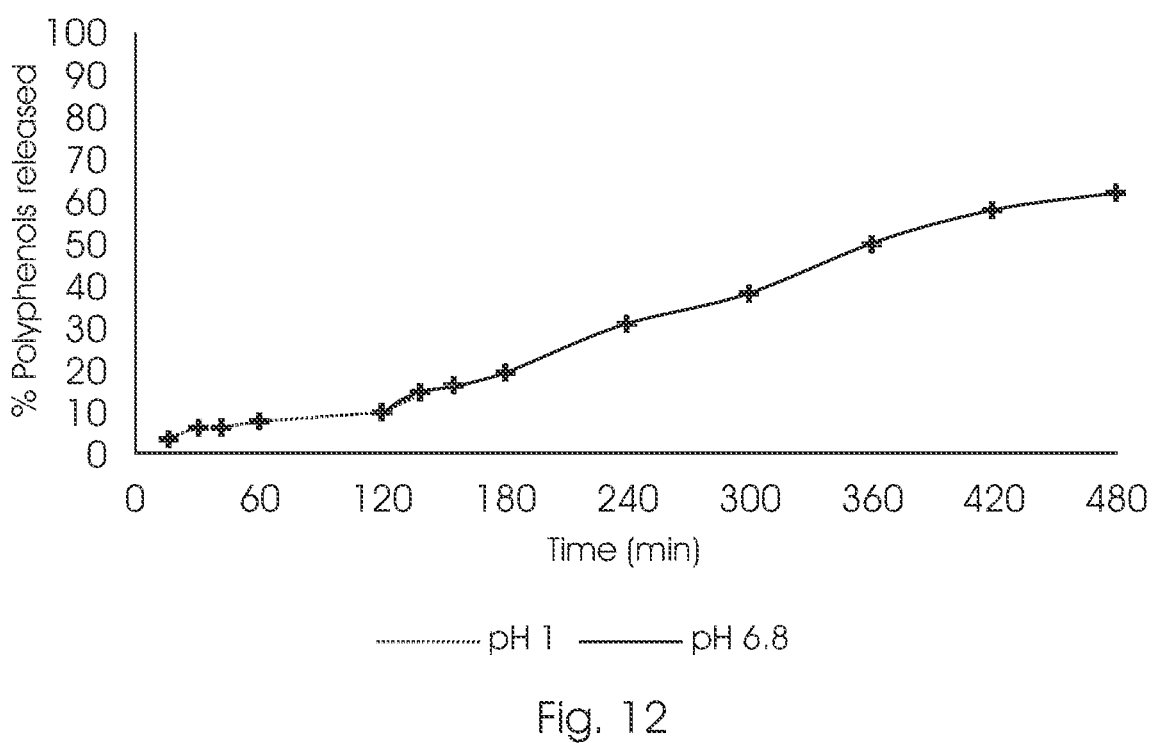
FIG. 12 shows a dissolution profile for Retalac® 3 sustained release mini-tablets.

The percentage release of total polyphenols plotted as a function of time for sustained release mini-tablets made of 20.4% hypromellose and lactose monohydrate (in equal parts) (Retalac®, R-3) is shown in FIG. 12. The dissolution profile in FIG. 12 shows a relatively slow release over the first 2 hours (acidic environment) followed by a faster release over the next 6 hours (neutral environment). The total polyphenol release was about 64% after 8 hours. This was an increase in the total amount of polyphenols released when compared to the Retalac® 2 formulation (R-2) of Example 6.

These formulations (K-3 and R-3) with the increased percentage Rooibos extract (and decreased percentage Kollidon SR© and Retalac®) substantially increased the dissolution rate of the respective formulations. Based on these results, two further formulations with a lower percentage of Kollidon SR® and Retalac© were prepared.

Example 11

Figure 13:
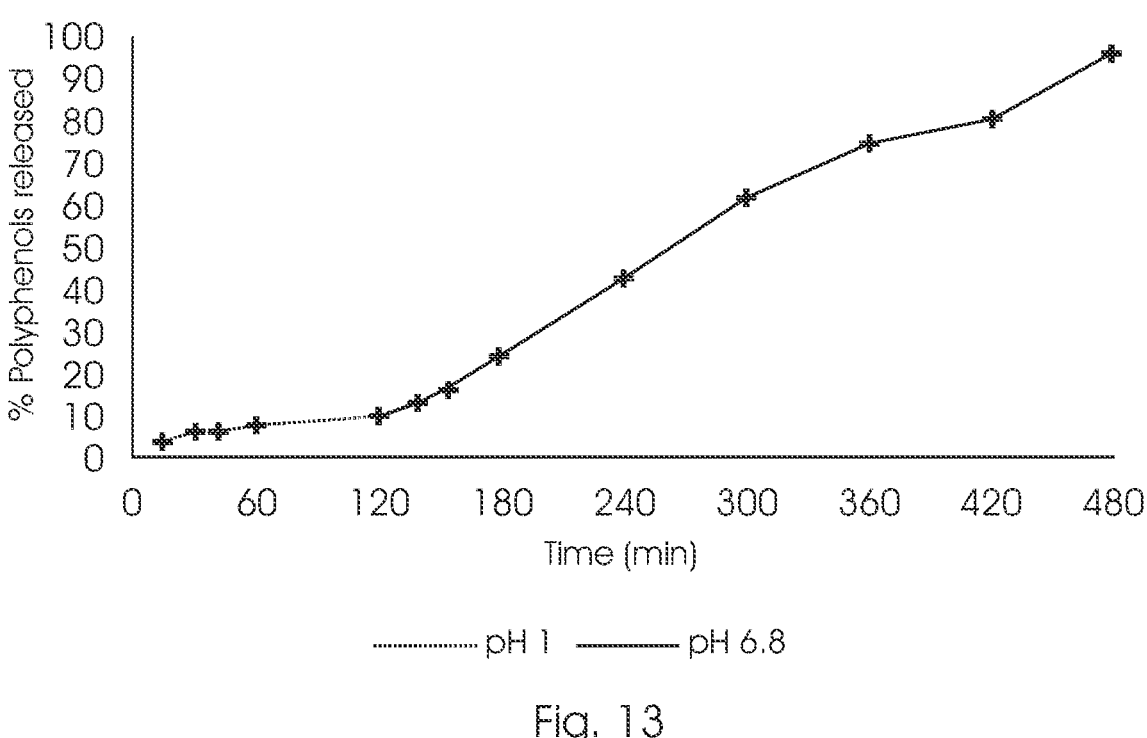
FIG. 13 shows a dissolution profile for Kollidon SR® 4 sustained release mini-tablets.

The percentage release of total polyphenols plotted as a function of time for sustained release mini-tablets made of 16.4% (w/w) polyvinyl acetate and polyvinylpyrrolidone (approximately 80:20 ratio) (Kollidon SR®, K-4) is shown in FIG. 13. The dissolution profile in FIG. 13 shows a relatively slow release over the first 2 hours (acidic environment) followed by a faster release over the next 6 hours (neutral environment). The total polyphenol release was about 96% after 8 hours. This was an increase in the total amount of polyphenols released when compared to the Kollidon SR® 3 (K-3) formulation of Example 9.

Example 12

Figure 14:
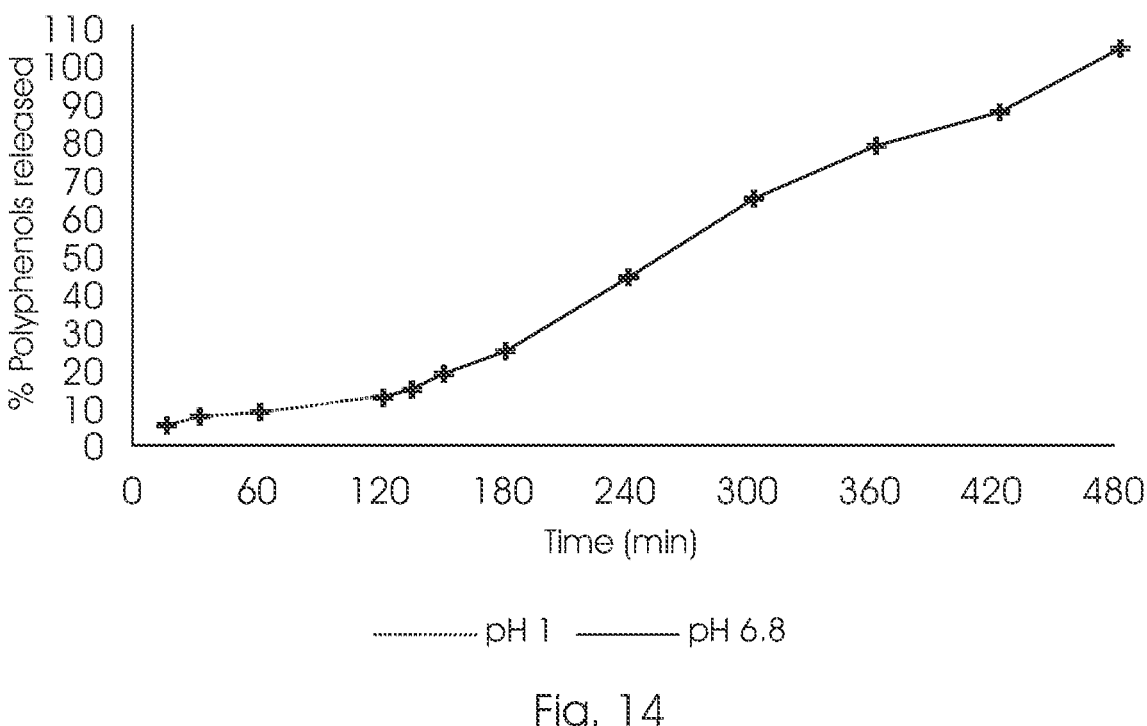
FIG. 14 shows a dissolution profile for Retalac® 4 sustained release mini-tablets.

The percentage release of total polyphenols plotted as a function of time for sustained release mini-tablets made of 15.4% (w/w) hypromellose and lactose monohydrate (in equal parts) (Retalac®, R-4) is shown in FIG. 14. The dissolution profile in FIG. 14 shows a relatively slow release over the first 2 hours (acidic environment) followed by a faster release over the next 6 hours (neutral environment). The total polyphenol release was about 105% after 8 hours. This was an increase in the total amount of polyphenols released when compared to the Retalac® 3 formulation (R-3) of Example 10.

The formulations containing either 16.4% Kollidon SR® or 15.4% Retalac® released the bulk of their polyphenol payloads in the eight-hour dissolution period. Production scale batches of these two formulations were prepared. Both formulations showed picking, which could be the result of heat build-up in the punches and the die during the increased run time. One way to overcome this is to increase the amount of lubricant in the formulation. The amount of magnesium stearate was adjusted from 0.1% to 0.25% (w/w). These formulations (K-5 and R-5) were prepared to evaluate the effect of the increased magnesium stearate on the dissolution of the formulations since magnesium stearate is hydrophobic and decreases the rate of dissolution of drugs in solid dosage forms.

Example 13

Figure 15:
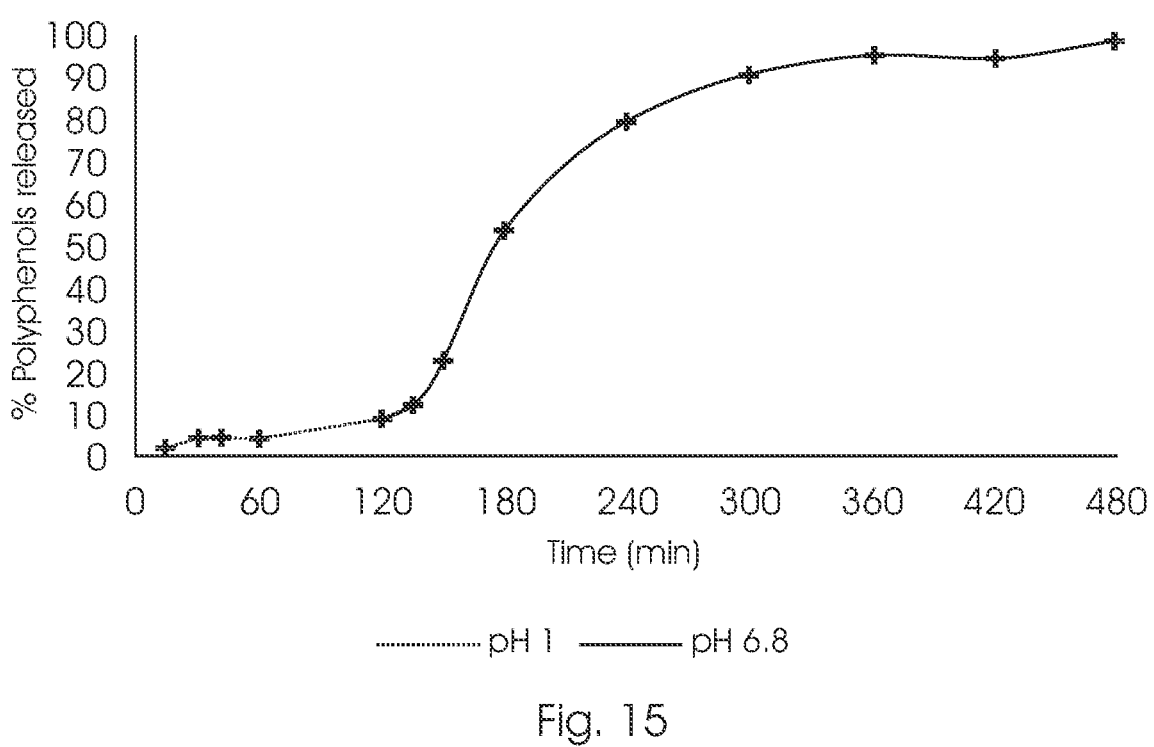
FIG. 15 shows a dissolution profile for Kollidon SR® 5 sustained release mini-tablets.

The percentage release of total polyphenols plotted as a function of time for sustained release mini-tablets made of 16.25% (w/w) polyvinyl acetate and polyvinylpyrrolidone (approximately 80:20 ratio) (Kollidon SR®, K-5) is shown in FIG. 15. The dissolution profile in FIG. 15 shows a relatively slow release over the first 2 hours (acidic environment) followed by a faster release over the next 6 hours (neutral environment). The total polyphenol release was about 97% after 8 hours. This was a similar amount of polyphenols released when compared to the Kollidon SR® 4 formulation (K-4) of Example 11, but the rate of dissolution increased substantially at the change of the pH and started to plateau after 3 hours in the neutral pH.

Therefore, based on the examples containing polyvinyl acetate and polyvinylpyrrolidone (approximately 80:20 ratio), it is envisaged that the sustained release component can comprise from about 10% to about 25%, preferably from about 12.5% to about 23%, and most preferably from about 16% to about 21.5% (w/w) polyvinyl acetate and polyvinylpyrrolidone (approximately 80:20 ratio).

Example 14

Figure 16:
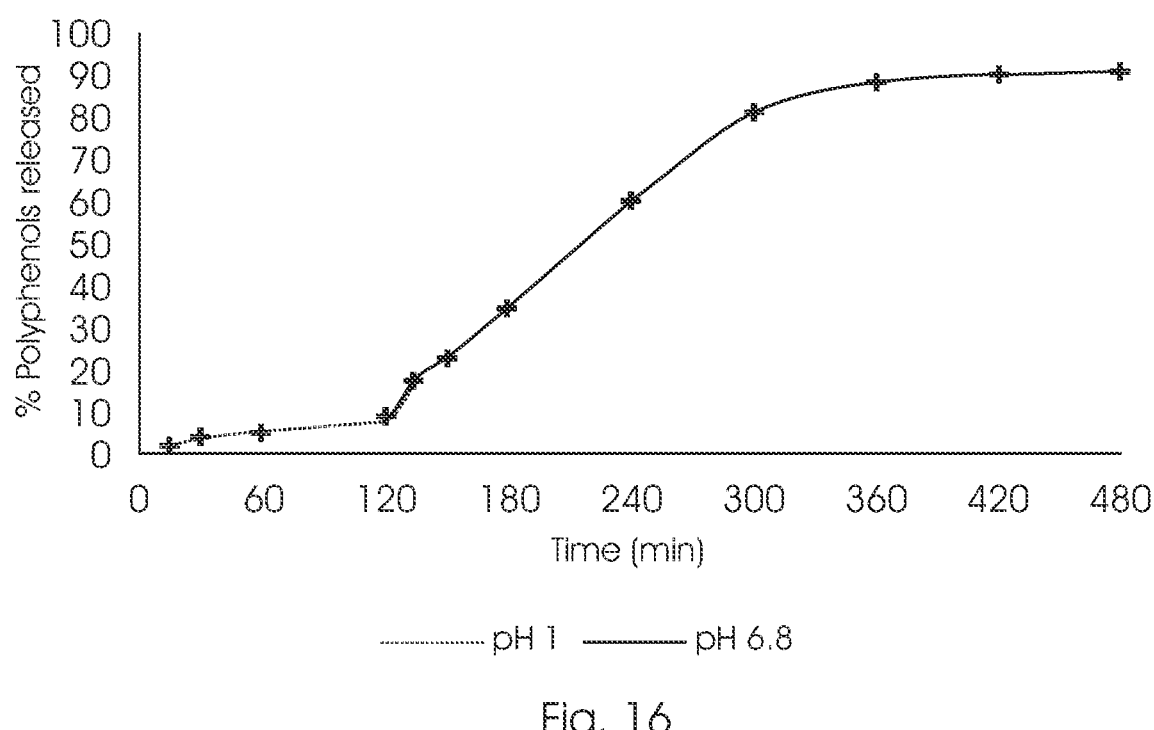
FIG. 16 shows a dissolution profile for Retalac® 5 sustained release mini-tablets.

The percentage release of total polyphenols plotted as a function of time for sustained release mini-tablets made of 15.25% (w/w) hypromellose and lactose monohydrate (in equal parts) (Retalac®, R-5) is shown in FIG. 16. The dissolution profile in FIG. 16 shows a relatively slow release over the first 2 hours (acidic environment) followed by a faster release over the next 6 hours (neutral environment). The total polyphenols released was about 91% after 8 hours. This was a similar amount of polyphenols released when compared to the Retalac® 4 (R-4) formulation of Example 12. Although still considered acceptable, this formulation did not exhibit the rapid dissolution rate and plateauing that was seen in the Kollidon SR® 5 (K-5) of formulation (Example 13).

Therefore, based on the examples containing hypromellose and lactose monohydrate (in equal parts), it is envisaged that the sustained release component can comprise from about 10% to about 25%, preferably from about 12.5% to about 23%, and most preferably from about 15% to about 20% (w/w) hypromellose and lactose monohydrate (in equal parts).

Example 15 (N-1 with Modified Magnesium Stearate Concentration)

Figure 17:
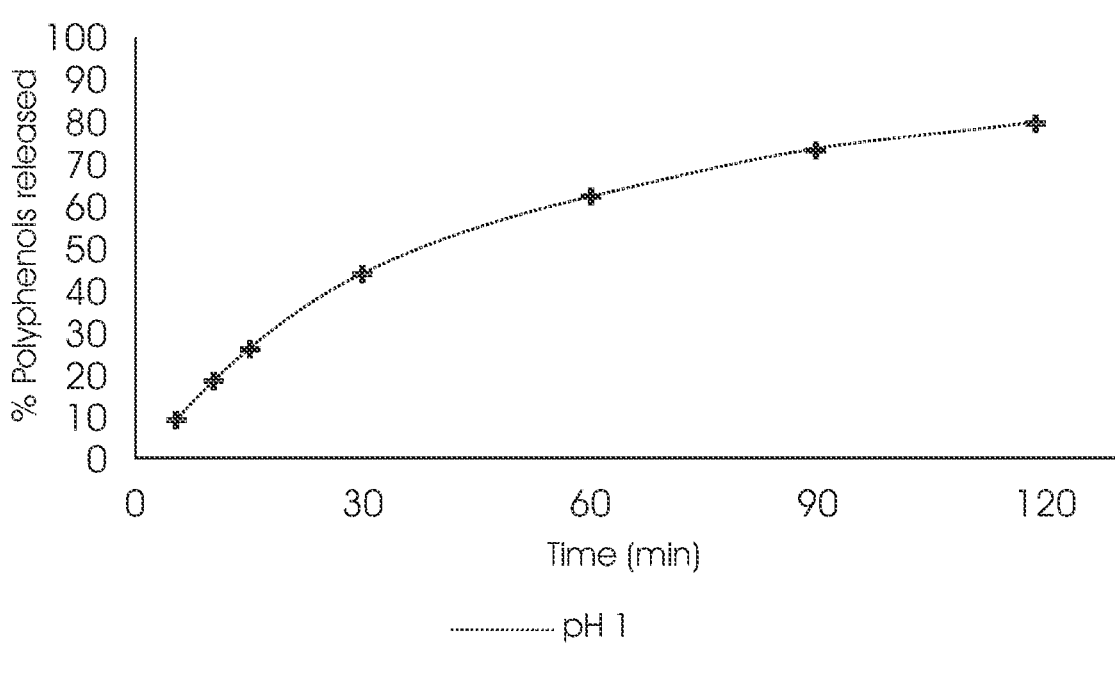
FIG. 17 shows a dissolution profile for immediate release mini-tablets of example 8, modified with 0.5% (w/w) magnesium stearate.

The sodium bicarbonate formulation N-1 was further modified by decreasing the magnesium stearate concentration from 1% (w/w) to 0.5% (w/w), which increased the dissolution rate. The percentage of total polyphenols released plotted against time for this formulation is shown in FIG. 17: FIG. 17 shows a relatively rapid release with about 80% of polyphenols being released in 2 hours in acid solution.

Example 16 (Mini-Tablet-In-Capsule Formulation)

Gelatine capsules were filled with two immediate release mini-tablets of Example 15 (modified N-1) and eight sustained release mini-tablets of Example 14 (R-5).

Figure 18:
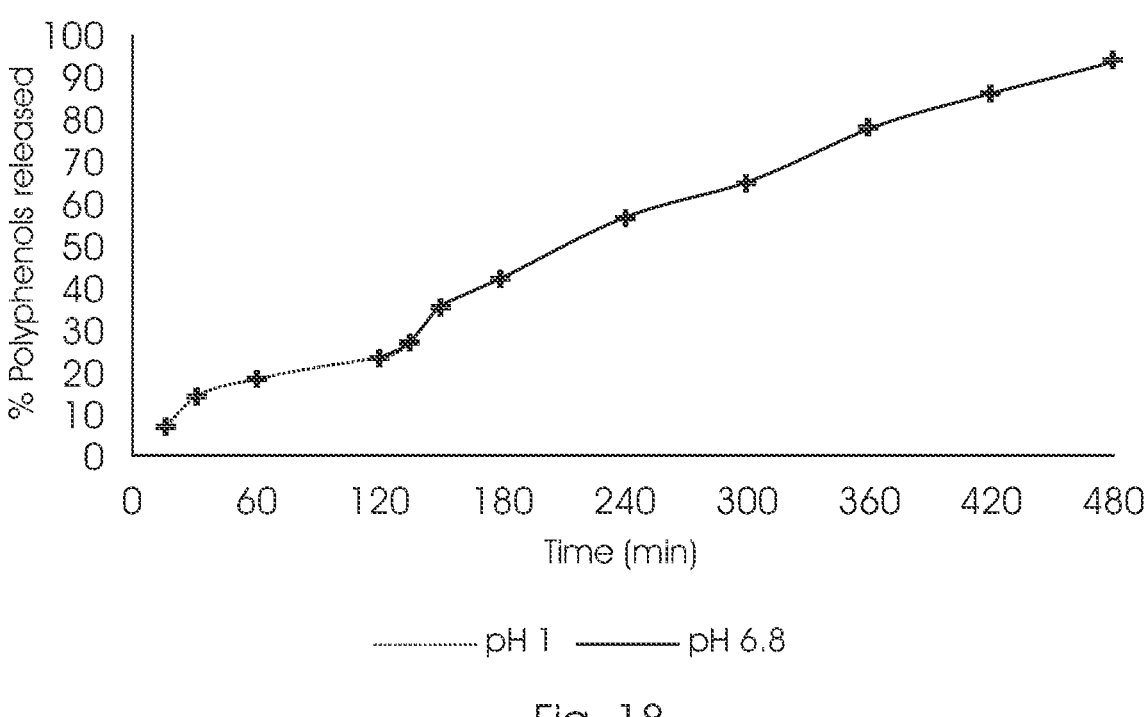
FIG. 18 shows a dissolution profile for a mini-tablet-in-capsule system containing two immediate release mini-tablets of example 15 and eight sustained release mini-tablets of example 14.

FIG. 18 shows the plot of the percentage polyphenols released against time for this mini-tablet-in-capsule formulation. The dissolution test was performed using 6 capsules and a substantially linear dissolution curve was obtained with a release of about 93.5% of the Rooibos polyphenols (SD=10.06) in 8 hours.

It will be appreciated that the above exemplifications of the invention may vary without departing from the spirit and/or the scope of the invention. It is easily understood from the present application that the particular features of the present invention, as generally described and exemplified, can be arranged and designed according to a wide variety of different configurations. In this way, the description of the present invention and the related examples are not provided to limit the scope of the invention but simply represent selected embodiments.

The skilled person will understand that the technical characteristics of a given embodiment can in fact be combined with characteristics of another embodiment, unless otherwise expressed or it is evident that these characteristics are incompatible. Also, the technical characteristics described in a given embodiment can be isolated from the other characteristics of this embodiment unless otherwise expressed.

REFERENCES

BELWAL, T., DHYANI, P., BHATT, I. D., RAWAL, R. S. & PANDE, V. 2016. Optimization extraction conditions for improving phenolic content and antioxidant activity in *Berberis asiatica* fruits using response surface methodology (RSM). *Food Chemistry,* 207, 115-124.

SINGLETON, V. L. & ROSSI, J. A. 1965. Colorimetry of Total Phenolics with Phosphomolybdic-Phosphotungstic Acid Reagents. *American Journal of Enology and Viticulture,* 16, 144-158.

USP. 2016d. United States Pharmacopeia 711: Dissolution. North Bethesda, Maryland, United States: United States Pharmacopeia Convention.

What is claimed is:

1. A multi-unit pharmaceutical composition comprising:

a. an immediate release component comprising:

a polyphenol-containing *Aspalathus linearis* extract in an amount of about 60% to about 80% (% w/w) of the immediate release component;

sodium bicarbonate in an amount of about 15% to about 30% (% w/w) of the immediate release component;

a disintegrant selected from sodium starch glycolate, sodium carboxymethyl cellulose, or mixtures thereof;

magnesium stearate in an amount of about 0.5% to about 1.0% (% w/w) of the immediate release component; and optionally one or more pharmaceutically acceptable excipients; and b. a sustained release component comprising:

a polyphenol-containing *Aspalathus linearis* extract in an amount of about 60% to about 80% (% w/w) of the sustained release component;

rate-controlling polymer excipients selected from the group consisting of polyvinyl acetate to polyvinylpyrrolidone in an approximately 80:20 mixture, hypromellose to lactose monohydrate in an approximately 50:50 mixture, and combinations thereof, wherein the rate controlling polymer excipients are present at a concentration of about 10% to about 25% (% w/w) of the sustained release component; and optionally one or more pharmaceutically acceptable excipients;

wherein the composition provides a substantially linear polyphenol release profile of at least about 80% to 90% over a predetermined period of up to 10 hours.

2. The composition according to claim 1, wherein the sodium bicarbonate is present at a concentration of about 24% (% w/w) or less in the immediate release component.

3. The composition according to claim 1, wherein the pharmaceutically acceptable excipients in the sustained release component include a binder.

4. The composition according to claim 3, wherein the binder is vinylpyrrolidone-vinyl acetate.

5. The composition according to claim 1, wherein the rate-controlling polymer excipient is polyvinyl acetate/polyvinylpyrrolidone which is present at a concentration of about 16% to about 22% (% w/w) of the sustained release component.

6. The composition according to claim 1, wherein the rate-controlling polymer excipients is hypromellose and lactose monohydrate which is present at a concentration of about 15% to about 21% (% w/w) of the sustained release component.

7. The composition according to claim 1, wherein the pharmaceutically acceptable excipients in the immediate and sustained release components include a lubricant.

8. The composition according to claim 7, wherein the lubricant is magnesium stearate.

9. The composition according to claim 1, wherein the predetermined period is about 6 hours to about 10 hours.

10. The composition according to claim 1, wherein the pharmaceutical composition is a mini-tablet-in-capsule system.

11. The composition according to claim 9, wherein the pharmaceutical composition contains 2 immediate release components and 8 sustained release components.

12. The composition according to claim 1 wherein each immediate release component has about the following composition, by mass percentage of the intermediate release component:

*Aspalathus linearis* extract: 66.7%,

Sodium bicarbonate: 24.3%,

Sodium starch glycolate: 8%, and

Magnesium stearate: 0.5%.

13. The composition according to claim 1, wherein each sustained release component has about the following composition, by mass percentage of the sustained release component:

*Aspalathus linearis* extract: 80%

Vinylpyrrolidone-vinyl acetate: 3.5%

Hypromellose and lactose monohydrate: 15.25%

Silica: 1%, and

Magnesium stearate: 0.25%.

14. The composition according to claim 1, wherein each sustained release component has about the following composition, by mass percentage of the sustained release component:

*Aspalathus linearis* extract: 80%

Vinylpyrrolidone-vinyl acetate: 3.5%

Polyvinyl acetate/polyvinylpyrrolidone: 15.25%,

Silica: 1%, and

Magnesium stearate: 0.25%.

15. A multi-unit pharmaceutical composition according to claim 1 for use in a method for providing a sustained release of polyphenols from an *Aspalathus linearis* source over a predetermined time period in a subject, the method comprising administering the multi-unit pharmaceutical composition to the subject, wherein the sustained release of polyphenols occurs according to a substantially linear polyphenol release profile.

16. A method for providing a sustained release of polyphenols from an *Aspalathus linearis* source over a predetermined time period in a subject, the method comprising administering a multi-unit pharmaceutical composition according to claim 1 to the subject, wherein the sustained release of polyphenols occurs according to a substantially linear polyphenol release profile.

* * * * *